(12) United States Patent
Shigemori et al.

(10) Patent No.: US 10,575,736 B2
(45) Date of Patent: Mar. 3, 2020

(54) BIOMETRIC INFORMATION ACQUISITION DEVICE

(71) Applicant: DAIKIN INDUSTRIES, LTD., Osaka-shi, Osaka (JP)

(72) Inventors: Kazuhisa Shigemori, Osaka (JP); Takehiko Hiei, Osaka (JP); Sayo Toramoto, Osaka (JP); Chiaki Tsuboi, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 16/099,495

(22) PCT Filed: May 13, 2016

(86) PCT No.: PCT/JP2016/002346
§ 371 (c)(1),
(2) Date: Nov. 7, 2018

(87) PCT Pub. No.: WO2017/195234
PCT Pub. Date: Nov. 16, 2017

(65) Prior Publication Data
US 2019/0104947 A1    Apr. 11, 2019

(51) Int. Cl.
*A61B 5/024* (2006.01)
*A61B 5/0456* (2006.01)
(Continued)

(52) U.S. Cl.
CPC ............ *A61B 5/024* (2013.01); *A61B 5/0456* (2013.01); *A61B 5/11* (2013.01); *A61B 5/16* (2013.01); *A61B 5/18* (2013.01)

(58) Field of Classification Search
None
See application file for complete search history.

(56) References Cited

U.S. PATENT DOCUMENTS 8,655,307 B1 * 2/2014 Walker .............. H04W 52/0212
455/405
9,738,125 B1 * 8/2017 Brickley ................. H04W 4/70
(Continued)

FOREIGN PATENT DOCUMENTS

CN          204218446 U      3/2015
JP          2010-46236 A     3/2010
(Continued)

OTHER PUBLICATIONS

International Search Report, issued in PCT/JP2016/002346, dated Jul. 19, 2016.
(Continued)

*Primary Examiner* — Tung S Lau
(74) *Attorney, Agent, or Firm* — Birch, Stewart, Kolasch & Birch, LLP

(57) ABSTRACT

A plurality of pulse position candidate extraction units characterize waves included in a vibration signal from a vibration sensor using predetermined specific forms and extract respective sets of pulse position candidates. A frequency distribution calculation unit calculates a frequency distribution of the pulse interval and a frequency distribution of variation in pulse intervals on each of the extracted sets of pulse position candidates. A distribution ratio calculation unit calculates the distribution ratio of a modal class to the total frequency in each of the calculated frequency distributions. A selection unit selects a set of pulse position candidates from among the extracted sets of pulse position candidates using the calculated relative frequencies as indicators for evaluating accuracy of the sets of pulse position candidates.

6 Claims, 11 Drawing Sheets

(51) Int. Cl.
*A61B 5/11* (2006.01)
*A61B 5/18* (2006.01)
*A61B 5/16* (2006.01)

(56) References Cited

U.S. PATENT DOCUMENTS

| | | |
|---|---|---|
| 2004/0210145 A1 | 10/2004 | Satoh et al. |
| 2008/0071177 A1 | 3/2008 | Yanagidaira et al. |
| 2010/0027769 A1* | 2/2010 | Stevens ............... G06F 21/6218 379/88.17 |
| 2010/0332171 A1* | 12/2010 | Ueno ..................... G01D 5/266 702/71 |
| 2012/0010514 A1 | 1/2012 | Vrazic |
| 2013/0288805 A1* | 10/2013 | Osawa .................... A63F 13/10 463/43 |
| 2014/0120961 A1* | 5/2014 | Buck ....................... H04W 4/12 455/466 |
| 2018/0036534 A1* | 2/2018 | Shin ........................ A61N 1/04 |

FOREIGN PATENT DOCUMENTS

| | | |
|---|---|---|
| JP | 2012-24408 A | 2/2012 |
| JP | 2015-66319 A | 4/2015 |
| JP | 2015-66337 A | 4/2015 |
| JP | 2015-97638 A | 5/2015 |
| JP | 2016-86974 A | 5/2016 |
| TW | 200820939 A | 5/2008 |
| WO | WO 2005/112764 A1 | 12/2005 |
| WO | WO 2010-107092 A1 | 9/2010 |
| WO | WO 2014/185397 A1 | 11/2014 |

OTHER PUBLICATIONS

Written Opinion of the International Searching Authority, issued in PCT/JP2016/002346, dated Jul. 19, 2016.
Extended European Search Report dated Nov. 7, 2019 in corresponding European Patent Application No. 16901583.1.

* cited by examiner (a)

(b)

ELECTROCARDIOG
RAM WAVEFORM

VIBRATION SIGNAL
(BODY MOVE SIGNAL)
OF VIBRATION SENSOR

BIOMETRIC INFORMATION ACQUISITION DEVICE

TECHNICAL FIELD

The present invention relates to a biometric information acquisition device, particularly relates to a configuration for accurately detecting biometric information on a person.

BACKGROUND ART

A conventional biometric information acquisition device disclosed in Patent Document 1 detects a sign of drowsiness of a driver driving a vehicle and monitors his/her biometric conditions.

More specifically, the device described in Patent Document 1 has six small air pouches, which have no air circulation therebetween, dispersedly disposed over the entire surface of a backrest portion of a seat of the vehicle. One of the pouches located near the lumber area of the seated person has a sensor for measuring fluctuations in air pressure inside the pouch. Based on the measured fluctuations in air pressure, the device obtains time-sequence signal data including pulse waves of the aorta near the lumbar area of the seated person, provides signal processing on the time-sequence signal data, and detects a sign of drowsiness as biometric information.

CITATION LIST

Patent Document

PATENT DOCUMENT 1: Japanese Unexamined Patent Publication No. 2010-46236

SUMMARY OF THE INVENTION

Technical Problem

Other than a sign of drowsiness of a driver driving a vehicle, the biometric information on a subject includes fluctuations in the heart rate and fluctuations in the interval between heartbeats as important indicators. Fluctuations in the interval (the R-R interval) between large pulses called R-waves, which appear on an electrocardiogram measuring the state of heartbeats of a person, are used as one of important indicators for evaluating the stress level and the autonomic nervous system activity.

For example, a vibration sensor is installed to a chair or a bed to detect a vibration corresponding to the heartbeats of a subject seated in the chair or lying on his/her back on the bed. Use of a vibration signal from the vibration sensor allows detection of fluctuations in the heart rate and in the interval between pulses from the subject in an awake state. This manner facilitates acquisition of the stress level and the autonomic nervous system activity of the subject in a short time without putting a plurality of electrodes for electrocardiographic examination on the subject, without making the subject more aware of the situation, or without constraining the subject.

In this method, a vibration caused by the heartbeats of the subject is propagated in the chest, the back, the buttocks, and other parts inside the body, which mitigates a sharp steep component of the wave corresponding to an R-wave of the electrocardiogram. The vibration is therefore observed as a waveform resonated on the body trunk. This vibration includes breathing, moves, and the like of the subject other than heartbeats. For example, as illustrated in FIG. 12A, each R-wave has a sharp steep shape on the waveform of an electrocardiogram, whereas a wave corresponding to the R-wave on a vibration signal detected by the vibration sensor is less steep as illustrated in FIG. 12B.

It is therefore safe and preferable to extract a resonant frequency component (4 to 10 Hz) of the body trunk that is generated from the pulse, from the vibration signal detected by the vibration sensor using, for example, a bandpass filter and to extract a wave corresponding to an R-wave from the extracted body trunk resonant component.

As illustrated in FIG. 13A, a sharp waveform corresponding to the R-wave can be observed on the body trunk component extraction waveform (indicated by a solid curve) by filtering and extracting the body trunk component using a bandpass filer and the like. However, characteristics of a pulse may attenuate or disappear from the filtered body trunk component extraction waveform depending on the circumstances, as illustrated in FIG. 13B, which makes it difficult to accurately extract a wave corresponding to the R-wave of an electrocardiogram. On such a body trunk component extraction waveform as illustrated in FIG. 13B, a waveform having a comparatively large amplitude (or an extremum) and located in front of or behind a waveform corresponding to the R-wave is frequently misread and extracted as a waveform corresponding to the R-wave, which problematically reduces the accuracy of intervals (pulse intervals) between waveforms corresponding to R-waves.

In view of the foregoing background, it is an object of the present invention, which relates to a biometric information acquisition device including a vibration sensor for detecting a vibration signal including heartbeats of a person, to accurately extract a waveform corresponding to an R-wave on an electrocardiogram from the detected vibration signal and from a body trunk component extraction waveform generated from the vibration signal.

Solution to the Problem

In order to achieve the object, the present invention prepares a plurality of types of extraction processing for extracting a pulse waveform (a pulse position candidate) corresponding to an R-wave of an electrocardiogram, evaluates each set of pulse position candidates obtained through corresponding extraction processing using a predetermined evaluation indicator, and selects a set of pulse position candidates obtained through any one of the types of extraction processing.

To be more specific, a biometric information acquisition device of a first invention includes detection unit (VS) detecting a vibration including heartbeats of a person (S) and acquires his/her biometric information. The biometric information acquisition device includes: a plurality of types of candidate extraction units (38a to 38t) that extract respective sets of pulse position candidates from a target signal that is a signal relating to a vibration signal from the detection unit (VS), based on predetermined specific forms; a distribution calculation unit (39) that calculates a frequency distribution relating to a pulse interval on each of the sets of pulse position candidates extracted by the types of candidate extraction unit (38a to 38t); a distribution ratio calculation unit (40) that calculates the distribution ratio of a modal class to the total frequency on each of the frequency distributions calculated by the distribution calculation unit; and a selection unit (41) that selects a set of pulse position candidates extracted by one of the types of candidate extraction units (38*a* to 38*t*) using the relative frequencies calculated by the distribution ratio calculation unit (40) as indicators for evaluating accuracy of the sets of pulse position candidates.

In the first invention, when the detection unit detects a vibration including heartbeats of a person, the types of candidate extraction units each extract sets of pulse position candidates. The sets of pulse position candidates are evaluated based on the evaluation indicators, and the selection unit selects a set of pulse position candidates extracted by one of the types of candidate extraction units.

In this process, the frequency distribution calculation unit calculates a frequency distribution relating to the pulse interval on each of the sets of pulse position candidates. In the frequency distribution relating to the pulse interval, if many of the extracted pulse position candidates are positioned on waves corresponding to R-waves of an electrocardiogram, the distribution is more condensed. If many of the extracted pulse position candidates are positioned on waves positioned a wave or more remote from waves corresponding to R-waves (if "wave skip" described later occurs), the distribution is more dispersed. Such a frequency distribution includes, as illustrated in FIG. 7, a high mountain representing a modal class and low mountains located at the right and left sides of the modal class. In this frequency distribution, a distribution ratio of the modal class to the total frequency represents the quantity of the "wave skip" and reflects how often "wave skip" occurs. The calculated distribution ratio of the modal class therefore represents the degree of accuracy of the extracted set of pulse position candidates, and thus use of the distribution ratio of the modal class as an evaluation indicator allows selection of a more accurate set of pulse position candidates.

In a second invention, the distribution calculation unit (39) of the biometric information acquisition device calculates a frequency distribution of a pulse interval or a frequency distribution of variation in pulse intervals as the frequency distribution relating to the pulse interval.

In the second invention, if the frequency distribution relating to the pulse interval is a frequency distribution of the pulse interval, the distribution ratio of the modal class is used as an effective evaluation indicator for a short target time (the period necessary to acquire effective number of pieces of pulse interval data). If the frequency distribution is a frequency distribution of variation in pulse intervals, the distribution ratio of the modal class is used as an effective evaluation indicator regardless of the length of the target time.

In a third invention, the selection unit (41) of the biometric information acquisition device selects a set of pulse position candidates having the largest distribution ratio from among a plurality of relative frequencies calculated by the distribution ratio calculation unit (40).

In the third invention, the selection unit selects a frequency distribution having the largest distribution ratio of the modal class to the total frequency, in other words, from among a plurality of sets of pulse position candidates, the selection unit selects a set including the largest number of pulse position candidates extracted on waves corresponding to R-waves of an electrocardiogram. This manner allows a selection of the most accurate set of pulse position candidates.

In a fourth invention, the types of candidate extraction units (38*a* to 38*t*) of the biometric information acquisition device include first candidate extraction units (38*a* to 38*j*) extracting a set of pulse position candidates from a target signal that is a vibration signal from the detection unit (VS), and second candidate extraction units (38*k* to 38*t*) extracting a set of pulse position candidates from a body trunk component extraction signal generated by extracting a body trunk component from the vibration signal from the detection unit (VS).

In the fourth invention, the target signal from which sets of pulse position candidates are extracted includes two types of signals, which are a vibration signal from the detection unit and a body trunk component extraction signal generated from the vibration signal. This structure allows selection of a more accurate set of pulse position candidates from a plurality of sets of pulse position candidates having different frequency distributions.

In a fifth invention, the types of candidate extraction units (38*a* to 38*t*) of the biometric information acquisition device include an amplitude-extraction type candidate extraction units (38*a* to 38*d*, 38*g* to 38*j*, 38*k* to 38*n*, and 38*q* to 38*t*) that uses the amplitude of a wave as the predetermined specific form and an extremum-extraction type candidate extraction units (38*e*, 38*f*, 38*o*, and 38*p*) that uses an extremum of a wave as the predetermined specific form.

In the fifth invention, at least the amplitude of a waveform and an extremum of a waveform are used for extraction of a pulse position candidate, which allows selection of a more accurate set of pulse position candidates from a plurality of sets of pulse position candidates having different frequency distributions.

In a sixth invention, the biometric information acquisition device further includes fluctuation calculation unit (42) that calculates fluctuations in the pulse interval or in variation in pulse intervals based on the set of pulse position candidates selected by the selection unit (41) and stress level calculation unit (43) that calculates the stress level or the autonomic nervous system activity of a person (S) based on the fluctuations in the pulse interval or in variation in pulse intervals calculated by the fluctuation calculation unit (42).

In the sixth invention, the stress level or the autonomic nervous system activity of a person can be calculated and measured by a simple method using a detected vibration signal.

ADVANTAGES OF THE INVENTION

According to the first invention, the biometric information acquisition device uses the distribution ratio of a modal class to the total frequency as an evaluation indicator, thereby obtaining a more accurate set of pulse position candidates.

According to the second invention, a more accurate set of pulse position candidates can be obtained using the distribution ratio of the modal class in the frequency distribution of the pulse interval or the distribution of variation in pulse intervals as an evaluation indicator.

According to the third invention, a more accurate set of pulse position candidates can be selected by selecting a set including the largest number of pulse position candidates extracted on waves corresponding to R-waves of an electrocardiogram.

According to the fourth and fifth inventions, the more accurate set of pulse position candidates can be selected from a plurality of sets of pulse position candidates having different frequency distributions.

According to the sixth invention, the stress level or the autonomic nervous system activity of a person can be calculated and measured by a simple method using no electrocardiograms.

DESCRIPTION OF EMBODIMENTS

Embodiments of the present invention will be described in detail below with reference to the drawings. The following embodiments are essentially preferable examples and not intended to limit the present invention, the applications, or the scope of usage.

Embodiment

Figure 1:
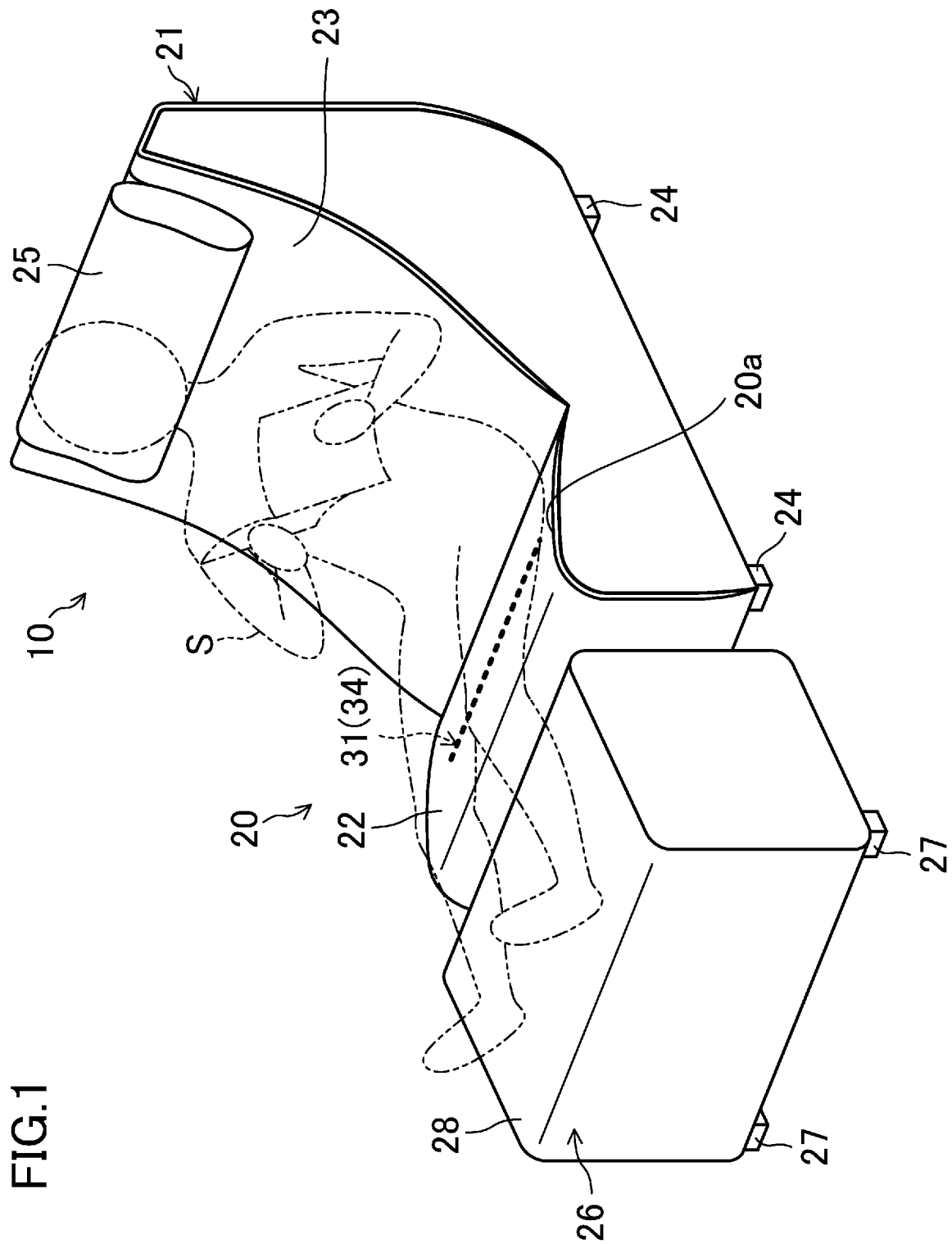
FIG. 1 is a schematic drawing of an overall configuration of a biometric information acquisition device according to an embodiment of the present invention.
Figure 2:
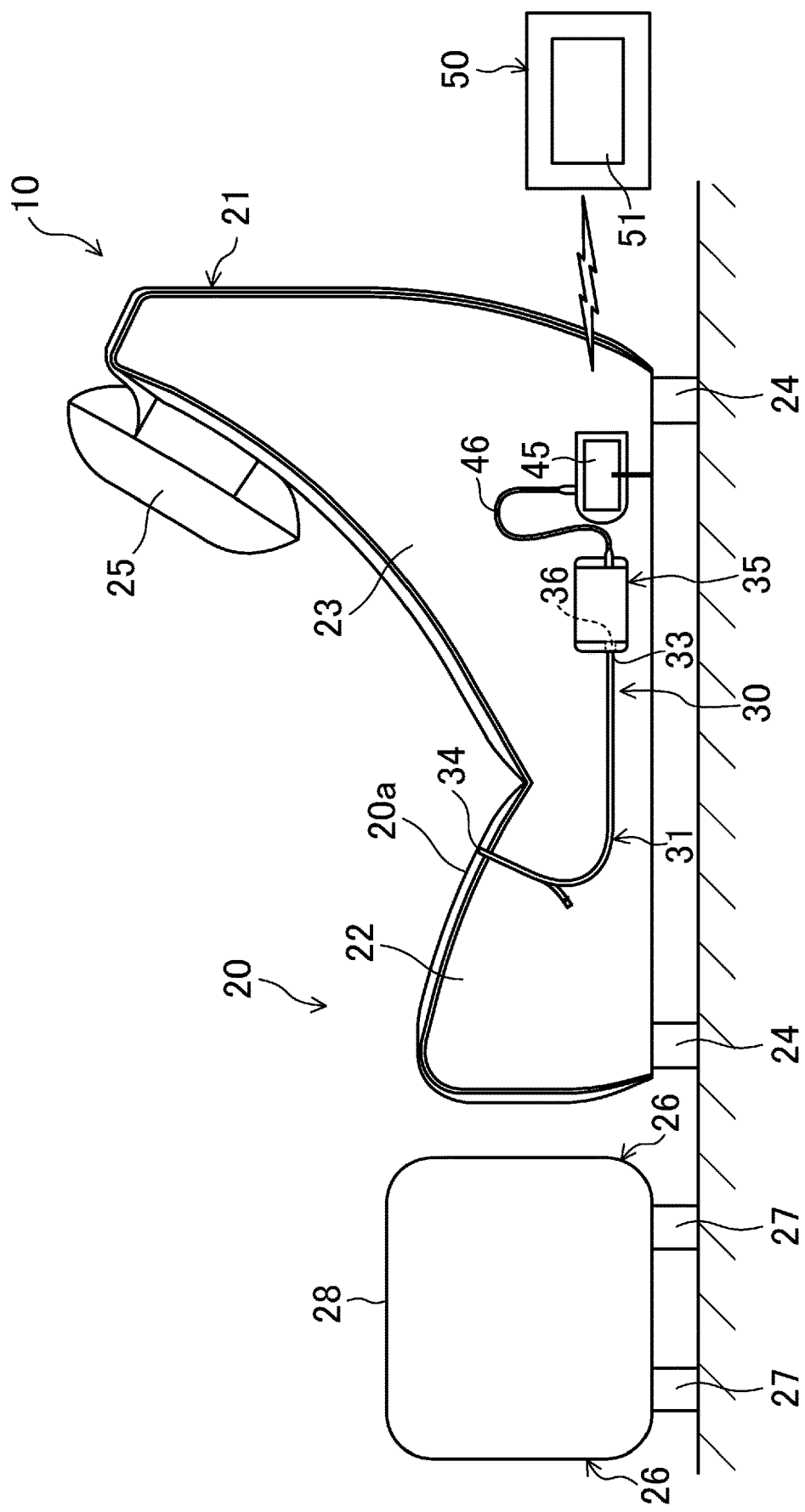
FIG. 2 is a schematic sectional view of the biometric information acquisition device.

FIGS. 1 and 2 are schematic drawings of a configuration of a biometric information acquisition device according to an embodiment of the present invention.

In FIGS. 1 and 2, a biometric information acquisition device (10) that acquires biometric information on a human body detects the stress level or the autonomic nervous system activity of a subject (a person) (S) as biometric information. The biometric information acquisition device (10) acquires fluctuations in the pulse interval or fluctuations in variation in pulse intervals from a body move including vibrations caused by heartbeats of the subject (S) and calculates the stress level or the autonomic nervous system activity of the subject (S).

As illustrated in FIGS. 1 and 2, the biometric information acquisition device (10) includes a sofa set (20), an information acquisition unit (30), a signal output unit (45), and a tablet terminal (50).

The sofa set (20) includes a single sofa (21) and an ottoman (26) placed in front of the sofa (21). The sofa (21) and the ottoman (26) have body surfaces covered by an artificial leather (20a) (for example, a polyurethane leather).

The sofa (21) includes a seating unit (22), a backrest unit (23) arranged behind the seating unit (22), and four legs (24) supporting the sofa (21).

The seating unit (22) has its surface inclined downward toward the rear part (a part close to the backrest unit (23)). On the seating unit (22), buttocks and thighs of the subject (S) are placed. On the backrest unit (23), the back and the head of the subject (S) are placed. The backrest unit (23) has its surface inclined upward toward the rear part. The sofa (21) includes the seating unit (22) and the backrest unit (23) arranged in a substantial V-shape. A cushion (25) is mounted to an upper part of the backrest unit (23) where the head of the subject (S) is located.

The ottoman (26) is a rectangular cuboid having its upper surface formed in a substantially square and is supported by the four legs (27). The ottoman (26) has, on its upper surface, a leg-rest surface (28) on which legs of the subject (S) are placed.

As illustrated in FIG. 2, the information acquisition unit (30) has a pressure-sensitive tube (31) and a sensor body (35).

The pressure-sensitive tube (31) is included in a pressure-sensitive unit that receives pressure generated by a body move of the subject (S). The pressure-sensitive tube (31) is made of a tube formed from resin (for example, polyvinyl chloride) and having an inner diameter of approximately 4 mm. The pressure-sensitive tube (31) has an end closed and the other end connected to the sensor body (35) through a connection unit (33). The intermediate portion of the pressure-sensitive tube (31) forms a pressure-sensitive unit body (a tube body (34)) disposed near a surface of the seating unit (22) of the sofa (21).

As illustrated in FIGS. 1 and 2, the tube body (34) is disposed near the surface of the seating unit (22) of the sofa (21). The tube body (34) extends straight in the width direction (the lateral direction) of the seating unit (22). The tube body (34) is arranged slightly closer to the rear part of the seating unit (22) from the intermediate portion of the seating unit (22) in the front-to-rear direction.

Figure 3:
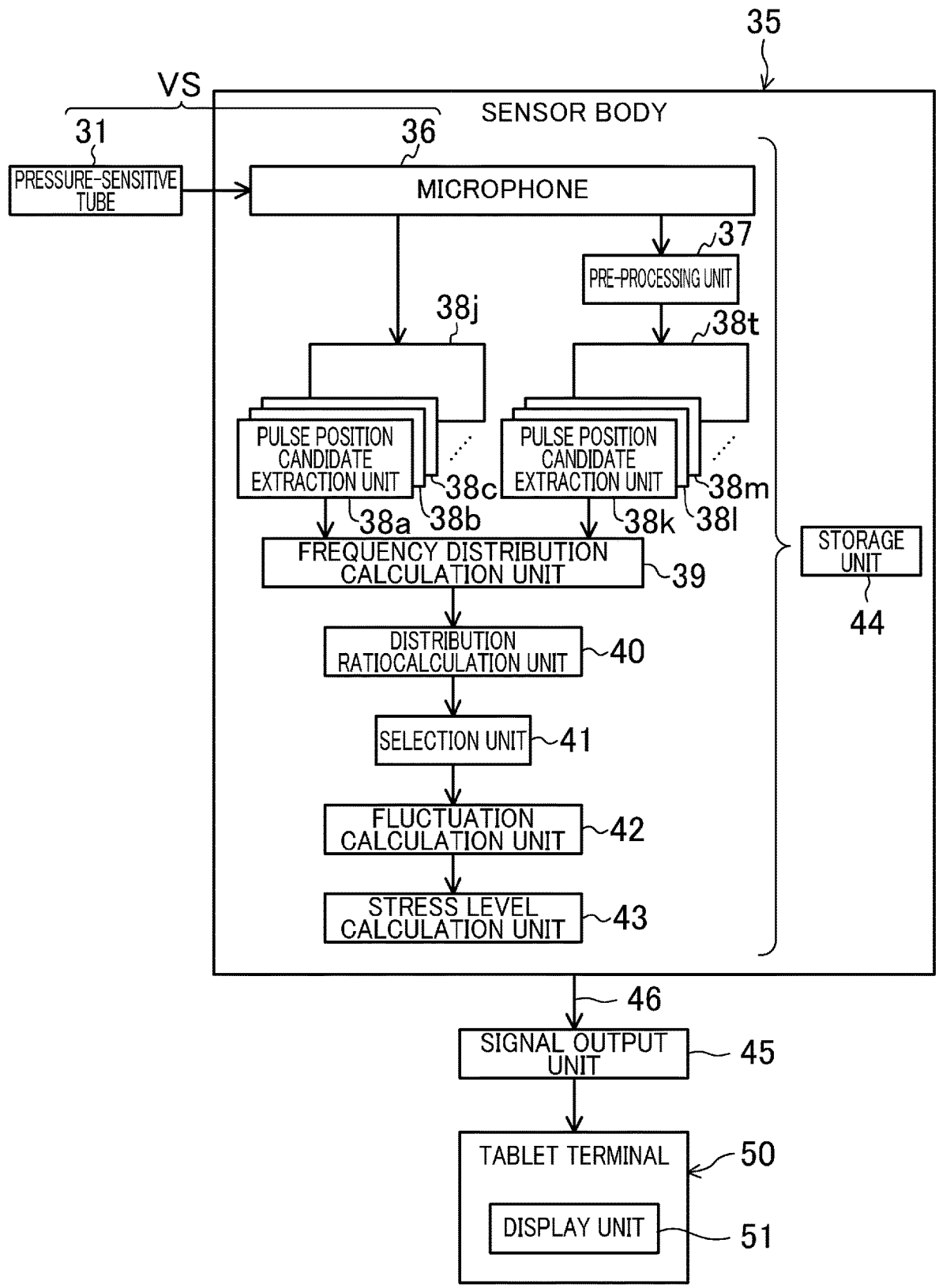
FIG. 3 is a block diagram illustrating a schematic configuration of a sensor body and its peripheral equipment included in the biometric information acquisition device.
Figure 12A:
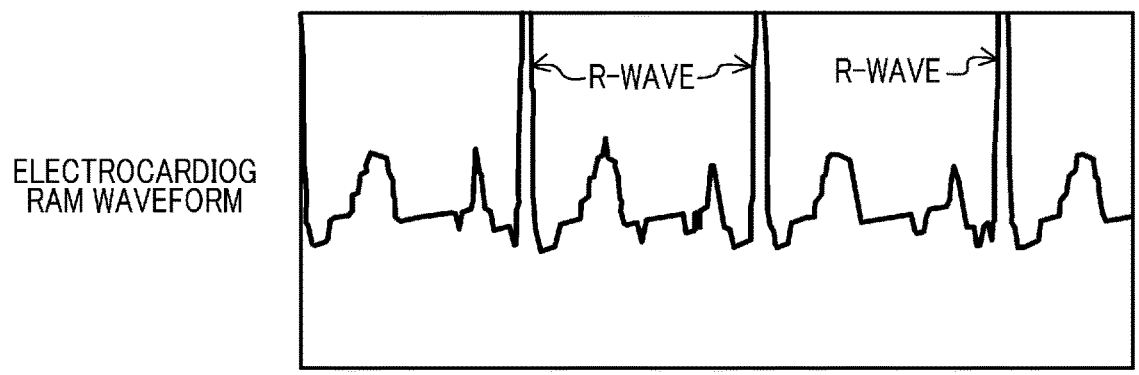
FIG. 12A is a graph of a waveform of an electrocardiogram.
Figure 12B:
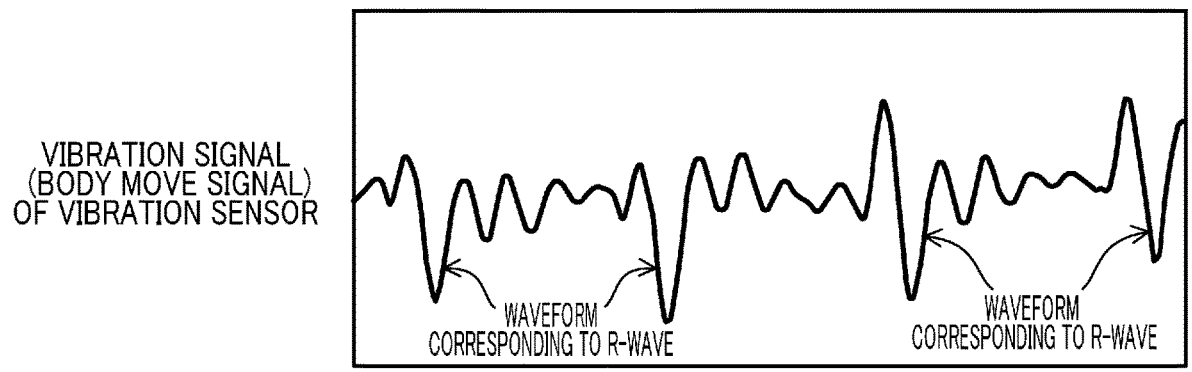
FIG. 12B is a graph of a waveform of a vibration signal from a vibration sensor.
Figure 13A:
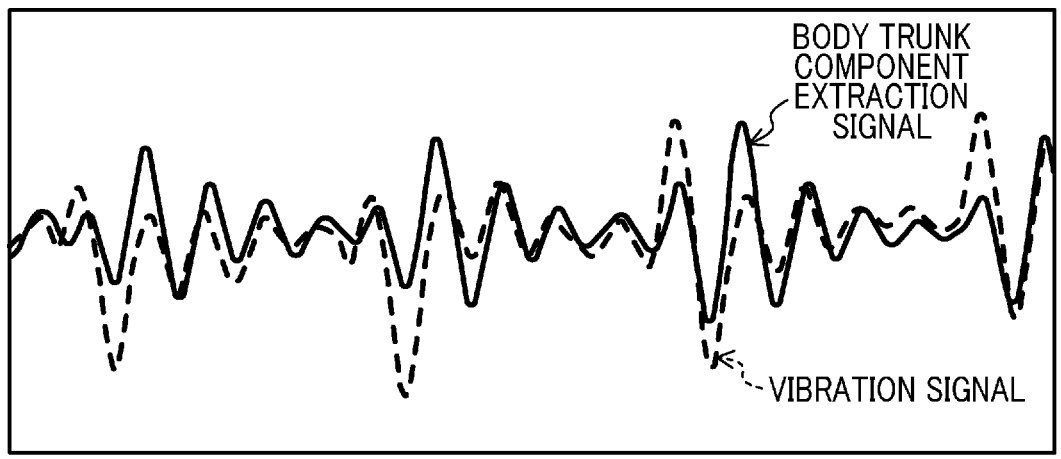
FIG. 13A is a graph in which waves corresponding to R-waves are desirably extracted from a body trunk component extraction signal.
Figure 13B:
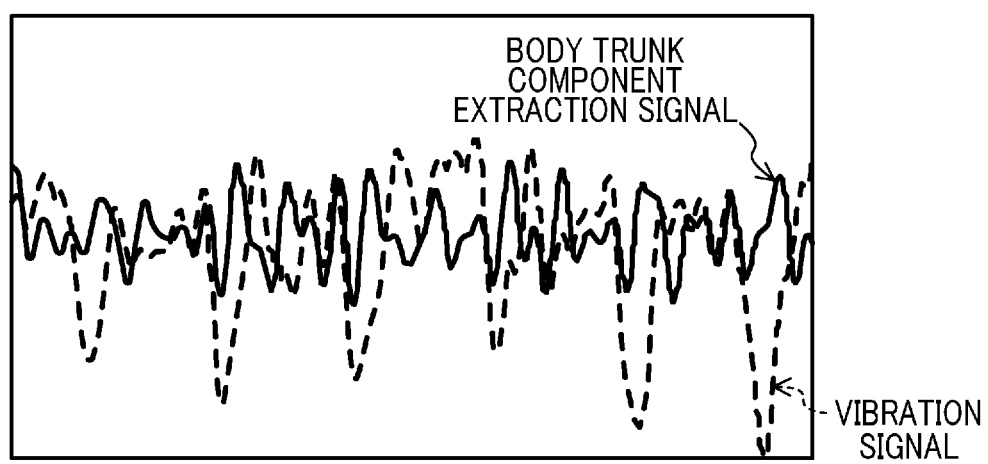
FIG. 13B is a graph in which waves corresponding to R-waves cannot be desirably extracted.

As illustrated in FIG. 3, the sensor body (35) is provided with a microphone (36) that detects the internal pressure of the pressure-sensitive tube (31). Upon detection of the internal pressure of the pressure-sensitive tube (31), the microphone (36) outputs a pressure signal. The pressure signal, detected by the microphone (36), from the internal pressure of the pressure-sensitive tube (31) is a vibration signal derived from a body move of the subject (S) and has a signal waveform as illustrated in FIG. 12B.

The pressure-sensitive tube (31) and the microphone (36) are included in a vibration sensor (VS) (detection unit) that detects a vibration signal derived from a body move of the subject (S).

As illustrated in FIG. 2, the sensor body (35) of the information acquisition unit (30) is connected to a signal output unit (45) through a cable (for example, an universal serial bus (USB) cable (46)). The signal output unit (45) is configured to wirelessly output a signal (for example, a later-described pulse interval and the stress level) output from the sensor body (35) to a tablet terminal (50). The signal output unit (45) may output a certain signal via wired connection instead of wireless connection. The tablet terminal (50) has a display unit (51) displaying the stress level and others calculated by the sensor body (35).

As illustrated in FIG. 3, the sensor body (35) includes a pre-processing unit (37), 20 pulse position candidate extraction units (38*a* to 38*t*), a frequency distribution calculation unit (39), a distribution ratio calculation unit (40), a selection unit (41), a fluctuation calculation unit (42), a stress level calculation unit (43), and a storage unit (44).

The internal configuration of the -described sensor body (35) will now be described in detail. The pre-processing unit (37) of the sensor body (35) extracts a resonant frequency component (4 to 10 Hz) of a body trunk generated from a pulse of the subject (S), from a vibration signal output from the microphone (36) using a bandpass filer and obtains a body trunk component extraction signal.

Ten (38*a* to 38*j*) out of 20 pulse position candidate extraction units receive a vibration signal, which is a body move signal, output from the microphone (36), and remaining ten pulse position candidate extraction units (38*k* to 38*t*) receive a body trunk component extraction signal output from the pre-processing unit (37). Each of 20 pulse position candidate extraction units (candidate extraction units) (38*a* to 38*t*) characterizes waves included in the received target signal in a corresponding predetermined manner, provides extraction processing for extracting vibration waveforms corresponding to R-waves of the electrocardiogram, and extracts a set of pulse position candidates.

Figure 4A:
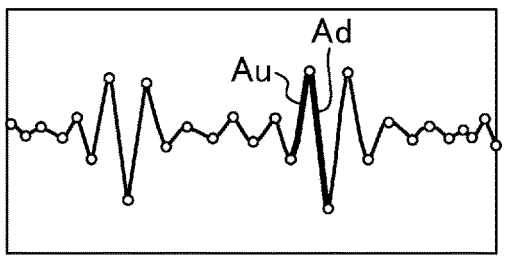
FIGS. 4A to 4J are graphs illustrating extraction processing (1 to 10) performed by pulse position candidate extraction units of the sensor body.
Figure 4B:
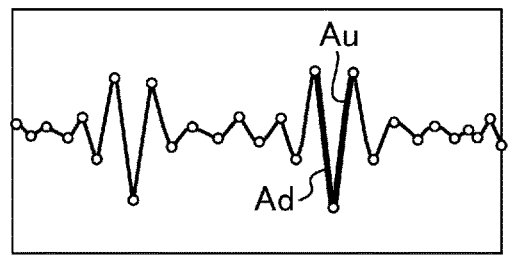

FIG. 4A to FIG. 4J illustrate extraction processing performed by the 20 pulse position candidate extraction units (38*a* to 38*t*). In extraction processing (1), as illustrated in FIG. 4A, the pulse position candidate extraction units (38*a* and 38*k*) characterize each waveform (an exemplary wave is depicted by a bold line in FIG. 4A) included in the signal with a mean amplitude Aa (a mean ((Au+Ad)/2) of an amplitude Au on the upward side and an amplitude Ad on the downward side of a mountain) of a mountain of the wave. In extraction processing (2), as illustrated in FIG. 4B, the pulse position candidate extraction units (38*b* and 38*l*) characterize each waveform in the signal with a mean amplitude Av (a mean ((Ad+Au)/2) of an amplitude Ad on the downward side and an amplitude Au on the upward side of a valley) of a valley of the wave.

Figure 4C:
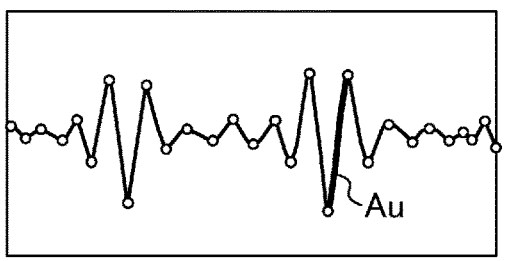
Figure 4D:
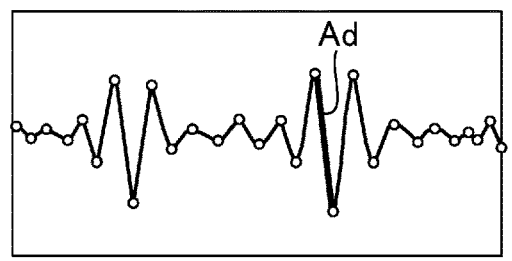
Figure 4E:
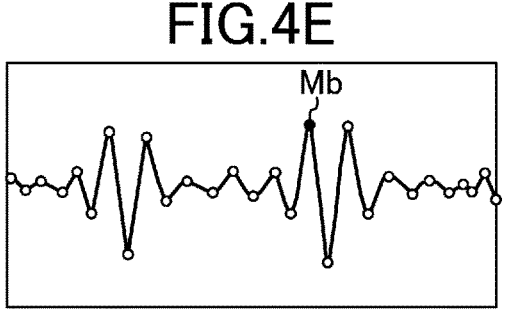
Figure 4F:
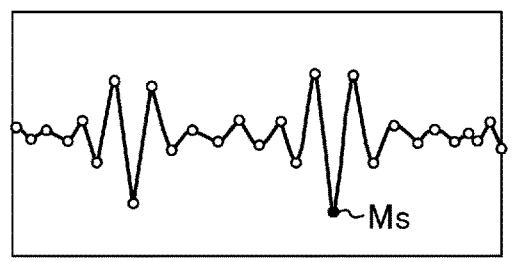

In extraction processing (3), as illustrated in FIG. 4C, the pulse position candidate extraction units (38*c* and 38*m*) characterize each waveform in the signal with an amplitude Au on the upward side of a mountain of the waveform. In extraction processing (4), as illustrated in FIG. 4D, the pulse position candidate extraction units (38*d* and 38*n*) characterize each waveform in the signal with an amplitude Ad on the downward side of a valley of the waveform. In extraction processing (5), as illustrated in FIG. 4E, the pulse position candidate extraction units (38*e* and 38*o*) characterize each waveform in the signal with a maximum Mb of the waveform. In extraction processing (6), as illustrated in FIG. 4F, the pulse position candidate extraction units (38*f* and 38*p*) characterize each waveform in the signal with a minimum Ms of the waveform.

Figure 4G:
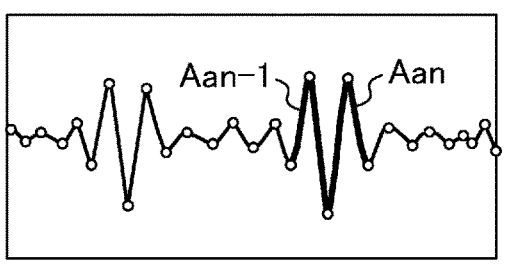
Figure 4H:
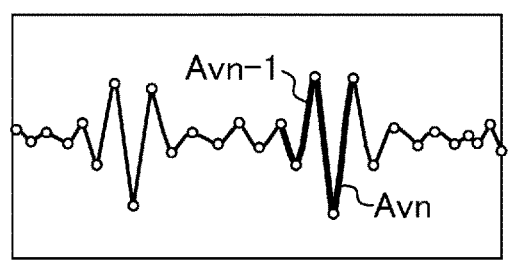
Figure 4I:
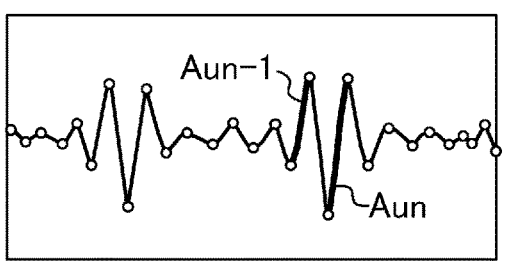
Figure 4J:
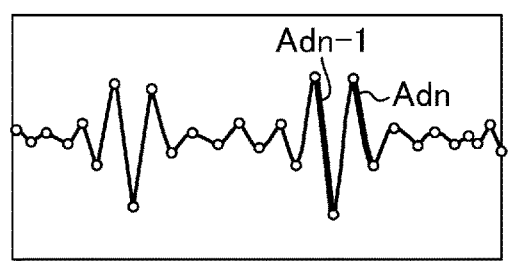

In extraction processing (7), as illustrated in FIG. 4G, the pulse position candidate extraction units (38*g* and 38*q*) characterize each waveform in the signal with a difference (Aan−Aan−1) between mean amplitudes Aan−1 and Aan of two adjacent mountains of waveforms, in other words, with a change in amplitude between two consecutive mountains. In extraction processing (8), as illustrated in FIG. 4H, the pulse position candidate extraction units (38*h* and 38*r*) characterize each waveform in the signal with a difference (Avn−Avn−1) between mean amplitudes Avn−1 and Avn of two adjacent valleys of waveforms, in other words, with a change in amplitude between two consecutive valleys. In extraction processing (9), as illustrated in FIG. 4I, the pulse position candidate extraction units (38*i* and 38*s*) characterize each waveform in the signal with a difference (Aun−Aun−1) between amplitudes on respective upward sides, Aun−1 and Aun, of two adjacent mountains. In extraction processing (10), as illustrated in FIG. 4J, the pulse position candidate extraction units (38*j* and 38*t*) characterize each waveform in the signal with a difference (Adn−Adn−1) between amplitudes on respective downward sides, Adn−1 and Adn, of two adjacent valleys.

In the extraction processing (1 to 10), each of the 20 pulse position candidate extraction units (38*a* to 38*t*) characterizes waveforms as described above and thereafter repeats, per predetermined period, processing of calculating the mean difference or the mean ratio between a wave and another wave located right before or right behind the wave or among three consecutive waves with the wave disposed in the middle, determining a wave having the largest mean difference or the largest mean ratio in the predetermined period to be a pulse position candidate, and extracting the determined wave.

Sixteen pulse position candidate extraction units (first candidate extraction units) (38*a* to 38*d*, 38*g* to 38*j*, 38*k* to 38*n*, and 38*q* to 38*t*) out of 20 pulse position candidate extraction units (38*a* to 38*t*) are defined as an amplitude-extraction type that determines a pulse position candidate using the amplitude of a wave as a determining feature. Remaining four pulse position candidate extraction units (second candidate extraction units) (38*e*, 38*f*, 38*o*, and 38*p*) are defined as an extremum-extraction type that determines a pulse position candidate using an extremum of a wave as a determining feature.

In FIG. 3, a frequency distribution calculation unit (distribution calculation unit) (39) of the sensor body (35) receives results of respective ten types of extraction processing (1 to 10) performed on a body move signal by the pulse position candidate extraction units (38*a* to 38*j*) and results of respective ten types of extraction processing (1 to 10) performed on a body trunk component extraction signal by the pulse position candidate extraction units (38*k* to 38*t*). On each of the results (sets of pulse position candidates) of the ten types of extraction processing on the body move signal, the frequency distribution calculation unit (39) repeatedly calculates the interval (a pulse interval) between two adjacent pulse position candidates, and further calculates a difference (variation) between the calculated pulse intervals, and creates a distribution of the variation. Likewise, on each of the results (sets of pulse position candidates) of the ten types of extraction processing on the body trunk component extraction signal, the frequency distribution calculation unit (39) calculates pulse intervals, and creates a distribution of variation in pulse intervals, and further creates a distribution of the pulse interval.

Figure 5:
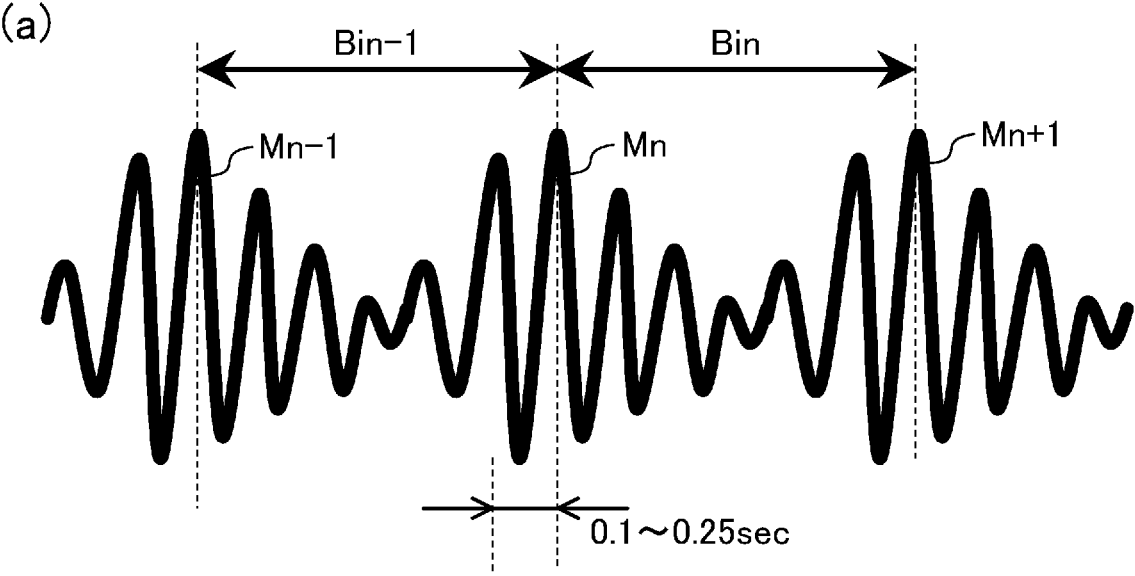
FIG. 5 An illustration (a) in FIG. 5 is a graph illustrating pulse position candidates correctly extracted, and an illustration (b) in FIG. 5 is a graph illustrating pulse position candidates when "wave skip" occurs.
Figure 5:
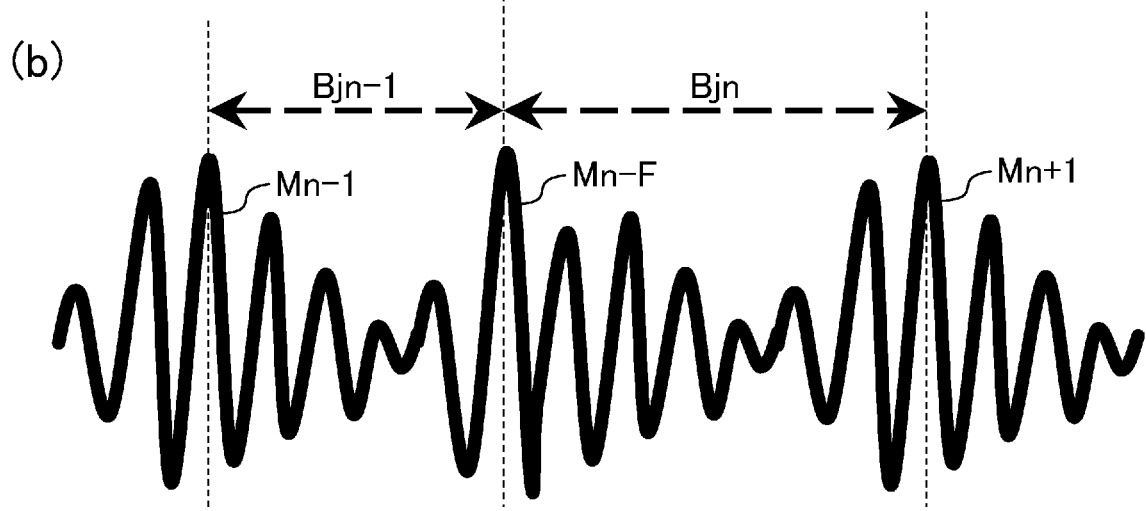
Figure 6:
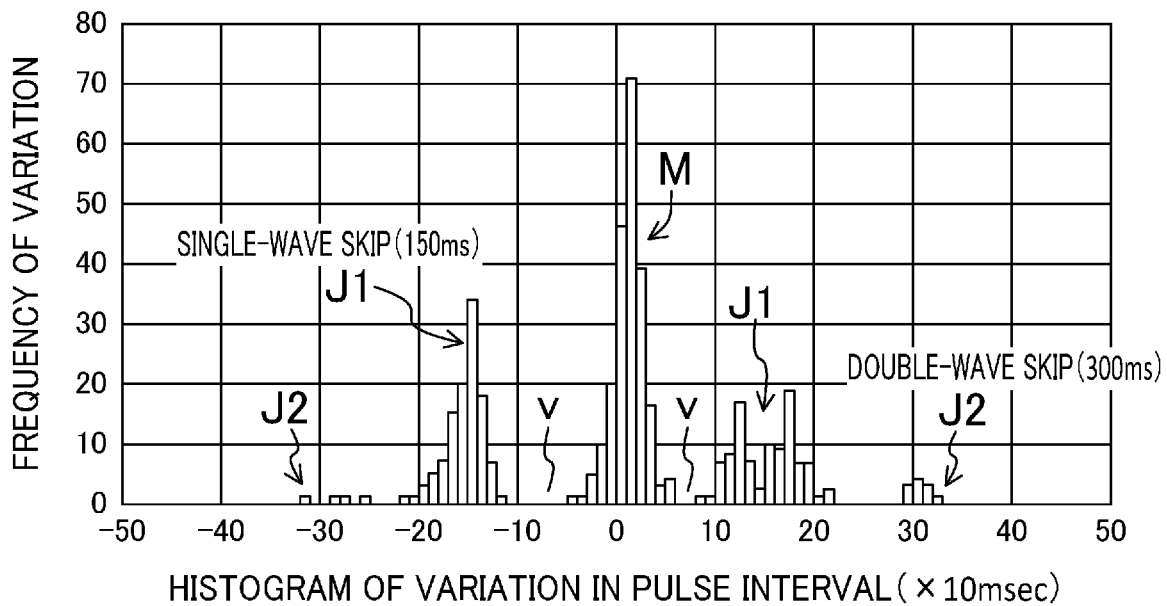
FIG. 6 is a chart illustrating a distribution of variation in pulse intervals when "wave skip" occurs.

Such a distribution of variation in pulse intervals and a distribution of the pulse interval calculated by the frequency distribution calculation unit (39) are in most cases the frequency distribution illustrated in FIG. 6. In extraction of a maximum wave having a largest amplitude or a maximum as described above, the posture of the subject (S) seated in the sofa (5) and a change in relative positional relation between the subject (S) and the vibration sensor (VS) may change the location of the extracted maximum wave. For example, in an illustration (a) of FIG. 5, three maximum waves (Mn−1), (Mn), (Mn+1), which are corresponding to R-waves of an electrocardiogram, are correctly extracted as pulse position candidates. In an illustration (b) of FIG. 5, for example, a difference in the posture of the subject (S) causes a pulse position candidate of a middle maximum wave (Mn−F) to shift to the position a wave before the pulse position candidate of the middle maximum wave (Mn) of the illustration (a) in FIG. 5. Such a shift in the position of a maximum wave will be referred to as "wave skip". In the presence of a plurality of such wave skips, in contrast to pulse intervals (Bin−1) and (Bin) having no occurrences of "wave skip" in the illustration (a) in FIG. 5, the pulse interval (Bin−1) is extracted short and the pulse interval (Bjn) is extracted long due to an occurrence of "wave skip" as illustrated in the illustration (b) in FIG. 5. In the presence of "wave skip", the distribution of variation in pulse intervals includes a modal class (M), which represents correct extraction of a wave corresponding to an R-wave of an electrocardiogram as a pulse position candidate, and further includes classes (J1) and (J2) as side peaks remote from the modal class (M) at each of the right side and the left side of the modal class (M), as illustrated in FIG. 6. The class (J1) next to the modal class (M) represents the frequency relating to variation when "single-wave skip" occurs, and the class (J2) next to the class (J1) represents the frequency relating variation when "double-wave skip" occurs.

For example, in the distribution of variation in pulse intervals, if a valley (V) is observed between the modal class (M) and the classes (J1) and (J2) located at each of the right side and the left side of the modal class (M), it can be determined that "wave skip" occurs. Pulse position candidates included in the classes (J1) and (J2) located outside the valley (V) thus can be regarded as candidates the wave data located in front of or behind required to be modified or discarded.

Figure 7:
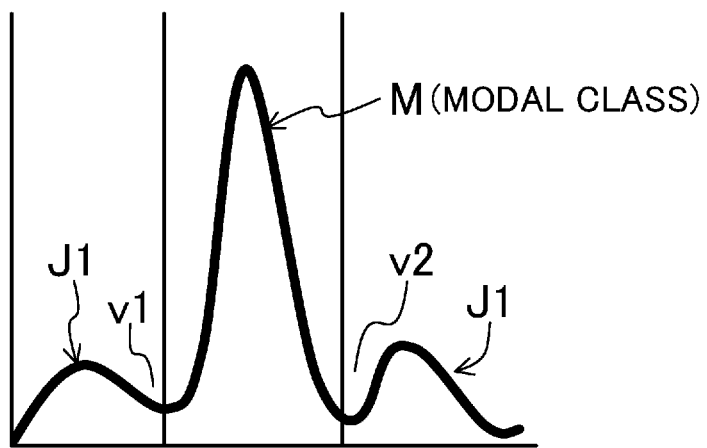
FIG. 7 is a graph illustrating calculation of a distribution ratio of a modal class to the total frequency in a distribution of variation in pulse intervals or in a distribution of the pulse interval.

The distribution ratio calculation unit (distribution ratio calculation unit) (40) of the sensor body (35) illustrated in FIG. 3 calculates the distribution ratio of the modal class to the total frequency in each of the 20 distributions of variation in pulse intervals and ten distributions of the pulse interval calculated by the frequency distribution calculation unit (39). For example, in the frequency distribution (such as a distribution of the pulse interval) as illustrated in FIG. 7, the distribution ratio of the modal class is given by Fm/Ft, where Fm denotes the frequency (for example, pulse intervals) in the modal class (M) located between two valleys (v1 and v2) and Ft denotes the total frequency.

The selection unit (selection unit) (41) selects a set of pulse position candidates having the best distribution ratio from 30 relative frequencies calculated by the distribution ratio calculation unit (40), which consist of: ten relative frequencies of the modal class in the distributions of variation in pulse intervals created on the body move signal, ten relative frequencies of the modal class in the distributions of variation in pulse intervals created on the body trunk component extraction signal, and ten relative frequencies of the modal class in the distributions of the pulse intervals created on the body trunk component extraction signal.

The fluctuation calculation unit (fluctuation calculation unit) (42) calculates fluctuations in the pulse interval or fluctuations in variation in pulse intervals based on the selected set of pulse position candidates having the best distribution ratio. The calculation will be described later in detail.

The stress level calculation unit (stress level calculation unit) (43) calculates the stress level of the subject (S) based on the fluctuations in the pulse interval or the fluctuations in variation in pulse intervals calculated by the fluctuation calculation unit (42). The calculation will be described later in detail.

The storage unit (44) from time to time stores a vibration signal detected by the microphone (36), a set of pulse position candidates extracted by each of the pulse position candidate extraction units (38*a* to 38*t*), a distribution of the pulse interval or a distribution of variation in pulse intervals calculated by the frequency distribution calculation unit (39), 30 relative frequencies of the modal class calculated by the distribution ratio calculation unit (40), the best distribution ratio selected by the selection unit (41), the stress level calculated by the stress level calculation unit (43), and others. In another manner, the storage unit (44) may store only a vibration signal, and other indicators may be subsequently calculated.

Operation of the Sensor Body (35)

Operation of the sensor body (35) will now be described with reference to the operation flowchart of FIG. 8.

Figure 8:
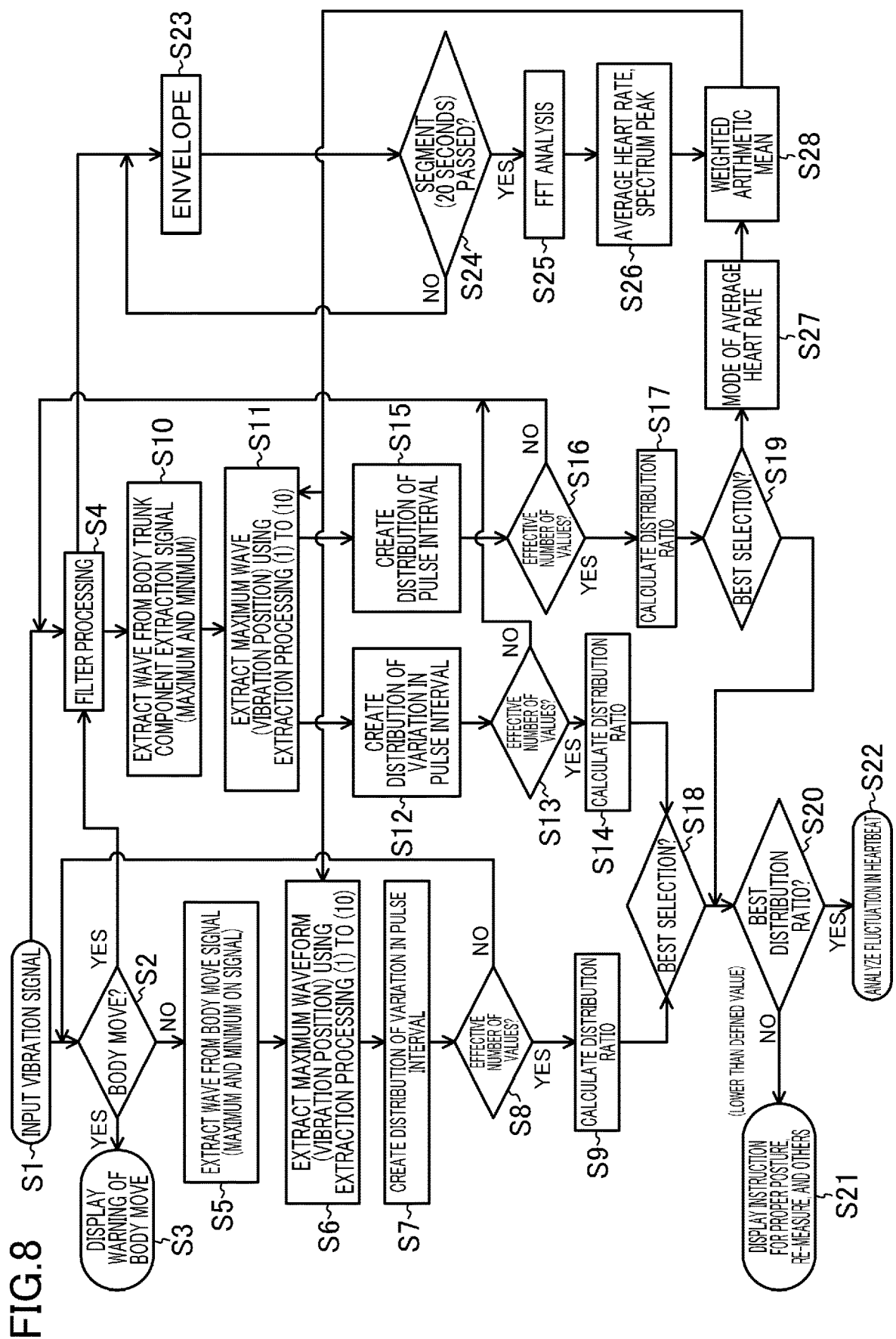
FIG. 8 is a flowchart illustrating operation of the sensor body.

In FIG. 8, the sensor body (35) inputs a vibration signal including heartbeats of the subject (S) and detected by the vibration sensor (VS), at Step S1. At Step S2, if the waveforms of the input vibration signal clearly indicate a move of the subject (S) such as laughing and nodding, the sensor body (35) regards the duration of the move as an invalid period and performs no signal processing in this period. Furthermore, upon determination of a body move, the sensor body (35) has the display unit (51) of the tablet terminal (50) display a warning that notifies of the body move, at Step S3. If it can be determined that the subject (S) has stood up from the sofa (21) based on, for example, disappearance of the input vibration signal, the sensor body (35) logs off the tablet terminal (50) with the personal data protected.

At Step S4, the sensor body (35) extracts a resonant frequency component (4 to 10 Hz) of a body trunk derived from the heartbeats, from the input vibration signal using a bandpass filter and obtains a body trunk component extraction signal. The sensor body does not extract the resonant frequency component of a body trunk for the duration of a body move, which is, in the invalid period of Step S2.

During a normal period with the subject (S) making no moves and being still at Step S2, at Step S5, the sensor body (35) performs the ten types of extraction processing (1 to 10) to extract waveforms corresponding to R-waves of an electrocardiogram based on the amplitude and an extremum from the vibration signal, which is, a body move signal representing a body move of the subject (S). At Step S6, on each type of extraction processing (1 to 10), the sensor body (35) repeatedly extracts maximum waveforms having the largest amplitude or a maximum from a plurality of neighboring waveforms and determines the extracted maximum waveforms to be a set of pulse position candidates.

For extraction of the maximum wave, a predetermined smallest cycle or a largest cycle is used for the initial (specifically, the time until the average heart rate is calculated) period. In use of the smallest cycle, on the assumption that no maximum waveforms or one maximum waveform is included in a cycle, a maximum shape is temporarily extracted in a target cycle. The maximum shape is compared with results of extraction of maximum waveforms in cycles before and behind the target cycle. Specifically, the position intervals therebetween and the extracted shapes are compared with one another. A result (a pulse position candidate) of extraction not to be regarded as the maximum shape in the cycle is discarded. In use of the largest cycle, on the assumption that a plurality of maximum waves are included in a cycle, a plurality of maximum shapes are extracted in a cycle, and pulse position candidates are temporarily determined in the order of size of the extracted maximum shapes. Among the pulse position candidates, a candidate having an abnormal interval (a too small interval) is discarded, and a certain number of maximum shapes are adapted as pulse position candidates.

At Step S7, the sensor body (35) calculates the interval between two adjacent pulse position candidates, and records a difference (variation) between the calculated pulse interval and another pulse interval as a result of previous calculation in the distribution of variation in pulse intervals. To evaluate the distribution pattern using smaller frequency, the distribution of variation in pulse intervals is created not by simply accumulating the frequency but by accumulating Gaussian distributions (the normal distributions) having a determined variance taking account of necessary resolution, an expected distribution range and frequency, and others. In this embodiment, the Gaussian distribution having standard deviation of σ±25 msec is used for a smoother distribution curve.

At Step S8, the sensor body (35) compares the frequency in the distribution of variation in pulse intervals with a predetermined number (effective number) of values. The effective number of values has a lower limit to reduce the influence of sporadic or low frequent arrhythmia, which appears even on a healthy subject (S), and further to accurately calculate the following distribution ratio. The lower limit is a period (a target time) of a vibration signal necessary to collect the lowest effective number of values, and in this case, a period including 30 or more heartbeats. The period is, for example, equal to or longer than 30 seconds, and preferably, equal to or longer than 60 seconds. In this embodiment, the frequency (the number of detected pulses) in 60 seconds is used as the effective number of values. For use in evaluation of a later-described distribution of the pulse interval, the upper limit is set at several to about ten minutes. More preferably, the evaluation is conducted with the period divided to reduce the influence of a change in the average heart rate of the subject (S). In this embodiment, periods corresponding to 0 to 100 seconds, 100 to 200 seconds, and 200 to 300 seconds, and the whole period of 0 to 300 seconds are employed as target periods of a vibration signal to collect the effective number of values. Each period described above is the time necessary to collect the effective number of values (the effective number of pulse intervals), and the period does not include a certain time in which an effective pulse interval cannot be collected due to, for example, a body move of the subject (S).

At above-mentioned Step S8, if the frequency is below the effective number of values, the sensor body (35) returns the process back to above-mentioned Step S2 to update the distribution of variation in pulse intervals. Upon obtaining a distribution of variation in pulse intervals having the frequency equal to or larger than the effective number of values, at Step S9, the sensor body (35) calculates the distribution ratio of the modal class to the total frequency for each of the effective numbers of values (the cumulative frequency in each of the periods of 0 to 100 seconds, 100 to 200 seconds, 200 to 300 seconds, and 0 to 300 seconds). Referring to the frequency distribution in FIG. 7 as an example, the distribution ratio is given by Fm/Ft, where Fm is the frequency (pulse intervals) of the modal class (M) located between two valleys (v1 and v2) and Ft is the total frequency.

In this manner, the sensor body (35) creates ten types of distribution of variation in pulse intervals on a vibration signal, which is, a body move signal. Likewise, at Step S10 to Step S14, the sensor body (35) performs the ten types of extraction processing (1 to 10) on the body trunk component extraction signal extracted at Step 4, extracts sets of pulse position candidates, creates ten types of distribution of variation in pulse intervals, and calculates the distribution ratio of the modal class to the total frequency in each of the distributions.

At above-mentioned Step S7 and Step S12, the sensor body (35) creates distributions of variation in pulse intervals. In addition, at Step S15, the sensor body (35) creates a distribution of the pulse interval from each of ten sets of pulse position candidates, which are extracted from the body trunk component extraction signal at Step S11, and updates the distribution. When the frequency reaches the effective number of values at Step S16, the sensor body calculates the distribution ratio of the modal class to the total frequency on each of the ten types of distribution of the pulse interval at Step S17, in the same manner as described above.

At Step S18, the sensor body (35) selects a distribution ratio having the largest value from among 20 relative frequencies obtained in the distributions of variation in pulse intervals and, at Step S19, selects a set of pulse position candidates having the best distribution ratio having the largest value from among ten relative frequencies obtained in the distributions of the pulse interval.

At Step S20, the sensor body (35) determines the best distribution ratio. If the value is lower than a defined value (the lower limit), for example, below 60% in value, the sensor body (35) determines that the determination of the stress level is difficult due to, for example, an improper seated posture of the subject (S) in the sofa (21). In this case, the sensor body (35) discards ten sets of pulse position candidates extracted through the extraction processing (1 to 10), and, at Step S21, has the display unit (51) of the tablet terminal (50) display a warning to instruct the subject (S) to sit in a proper posture. The sensor body (35) returns the process back to the beginning, and inputs a vibration signal from the vibration sensor (VS) again to measure the stress level.

Figure 9:
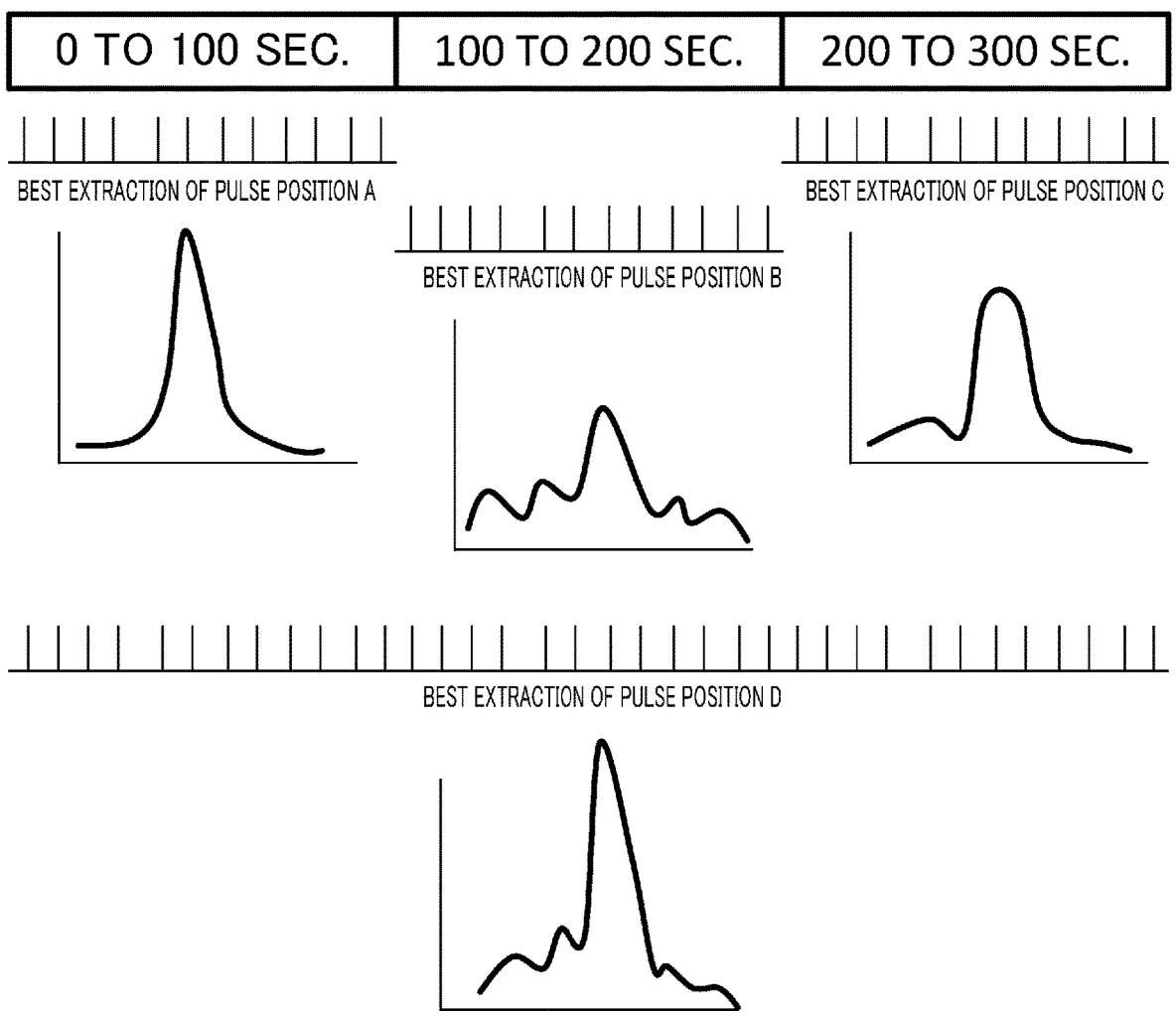
FIG. 9 illustrates graphs of exemplary frequency distributions having the best distribution ratios of modal classes in respective predetermined periods.

In the embodiment, for example as illustrated in FIG. 9, if the sensor body determines three consecutive periods including the period of 0 to 100 seconds, the period of 100 to 200 seconds, and the period of 200 to 300 seconds to have best relative frequencies (A), (B), and (C), in the extraction processing (1), (5), and (8), respectively, and further determines the whole period of 0 to 300 seconds to have the best distribution ratio (D) in the extraction processing (7), the sensor body (35) calculates a mean ((A+B+C)/3) of the three best relative frequencies (A) to (C) for 100 seconds, compares the mean with the best distribution ratio (D) for 300 seconds, and selects a larger distribution ratio at Step S18.

Upon selection of the best distribution ratio as described above, if the best distribution ratio is equal to or greater than the defined value (the lower limit), the sensor body (35) calculates fluctuations in heartbeats and judges the stress level of the subject (S) at Step S22. For calculation of fluctuations in heartbeats, the sensor body (35) conducts a frequency analysis of variation (fluctuations in the pulse intervals) in the pulse intervals by converting the set of pulse interval data (irregular time interval data) to regular time interval data using linear interpolation and further implementing a fast Fourier transform (FFT) on the pulse interval data having regular time intervals, and obtains the ratio (LH/HF) of a low frequency (LF) component (for example, 0.04 to 0.15 Hz) to a high frequency (HF) component (for example, equal to or greater than 0.15 Hz) relating to fluctuations in the pulse intervals. The sensor body has the display unit (51) display the ratio as an indicator for evaluating the stress level or the autonomic nervous system activity. The ratio (LH/HF) equal to or greater than a first predetermined value (for example, "2") allows to determine that the stress level is high. The ratio equal to or greater than a second predetermined value (for example, "5") allows to determine that the subject is under excessive stress.

Furthermore, at Step S23 to Step S28, the sensor body (35) performs processing to calculate the average heart rate of the subject (S) on the body trunk component extraction signal obtained at above-mentioned Step S4. At Step S23, the sensor body (35) creates an envelope of the body trunk component extraction signal. At Step S24, the sensor body (35) determines whether a predetermined segment (for example, a period corresponding to 20 seconds), which is used as an effective period for the body trunk component extraction signal, has passed. If the segment has not yet passed, the sensor body (35) returns the process back to Step S23 and continues to create the envelope. Once the predetermined segment has passed, the sensor body implements (35) a fast Fourier transform (FFT) at Step S25 and calculates the average heart rate and the height ratio between a first spectral peak and a second spectral peak at Step S26. At Step S27, the sensor body (35) calculates the mode of the average heart rate based on the set of pulse position candidates having the best distribution ratio selected at Step S19. The mode is given by: a distribution ratio/(1−the distribution ratio). At Step S28, the sensor body (35) weighs the average heart rate, the height ratio between the spectra, which are calculated at above-mentioned Step S26, and the mode of the average heart rate calculated at Step S27, and calculates the arithmetic mean of them, and determines the predetermined period (the cycle used for extraction of a maximum wave) used at the Step S6 and Step S11 based on the calculated average heart rate.

Effects of the Embodiment

Figure 10A:
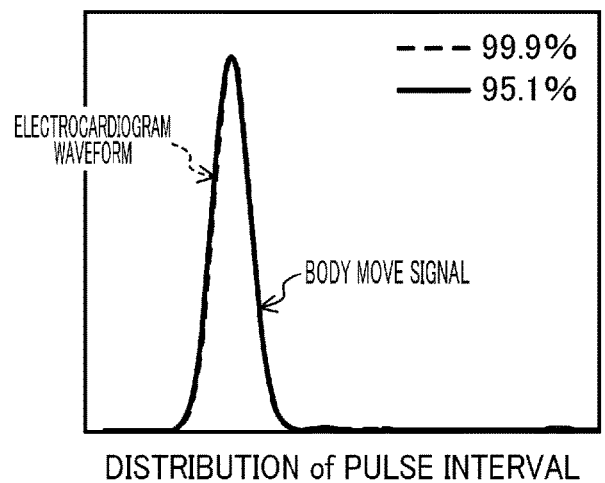
FIG. 10A is a graph of desirable distributions of pulse intervals on an electrocardiogram waveform and a body move signal when no "wave skip" occurs.
Figure 10B:
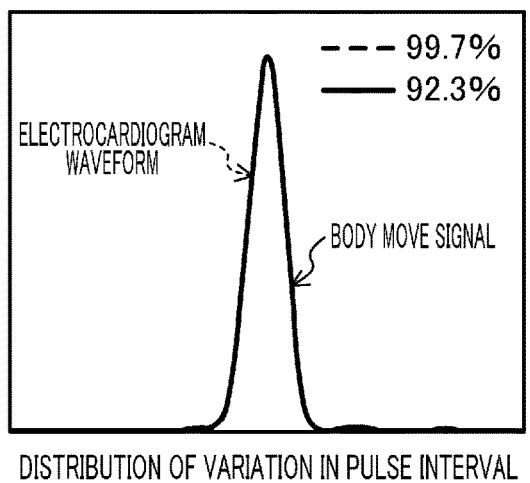
FIG. 10B is a graph of distributions of variation in pulse intervals under the same conditions.

In this embodiment, as described above, a distribution of variation in pulse intervals and a distribution of the pulse interval are created on a vibration signal from the vibration sensor (VS) based on a set of pulse position candidates extracted for the period of 300 seconds. If the distribution of variation in pulse intervals and the distribution of the pulse interval are desirable distributions having no occurrences of "wave skip", the respective distributions have narrow dispersion indicated by solid curves in FIGS. 10A and 10B and are similar with a distribution of variation in pulse intervals and a distribution of the pulse interval (indicated by broken curves in FIGS. 10A and 10B) created from an electrocardiogram. The distribution ratio of the modal class (M) to the total frequency is close to the distribution ratio of the modal class created from the electrocardiogram. For example, in the distributions of the pulse interval in FIG. 10A, the distribution ratio based on the vibration signal from the vibration sensor (VS) denotes 95.1% whereas the distribution ratio based on the electrocardiogram denotes 99.9%. In the distributions of variation in pulse intervals in FIG. 10B, the distribution ratio based on a vibration signal from the vibration sensor (VS) denotes 92.3% for that of 99.7% on the electrocardiogram.

Figure 11A:
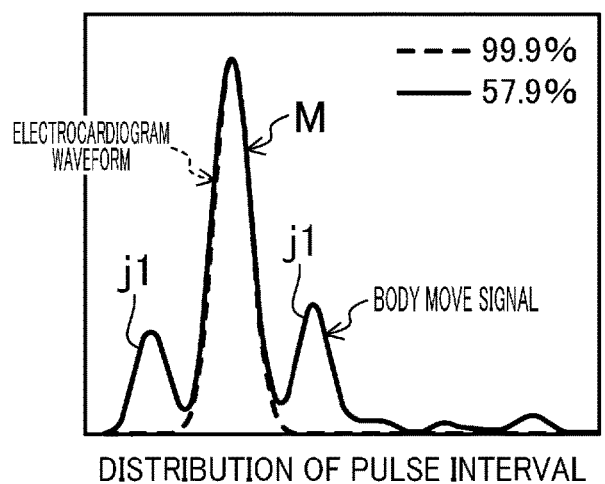
FIG. 11A is a graph of distributions of pulse intervals on an electrocardiogram waveform and a body move signal when "wave skip" occurs.
Figure 11B:
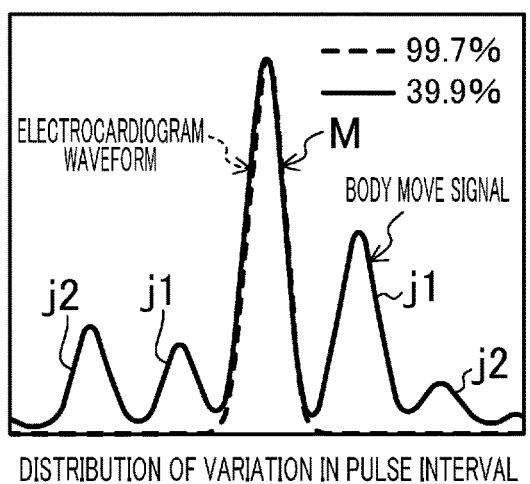
FIG. 11B is a graph of distributions of variation in pulse intervals under the same conditions.

On the other hand, as illustrated in FIG. 11A and FIG. 11B, each distribution (indicated by a solid curve) base on a vibration signal from the vibration sensor (VS) has occurrences of "wave skip" and thus includes a number of abnormal values. The distribution therefore has the class (j1) representing "single-wave skip" and/or the class (j2) representing "double-wave skip" next to the modal class (M). In this case, the distribution ratio of the modal class (M) is markedly lower than that based on an electrocardiogram (indicated by broken curves). For example, in the distributions of the pulse interval in FIG. 11A, the distribution ratio based on a vibration signal from the vibration sensor (VS) denotes 57.9% whereas the distribution ratio based on an electrocardiogram denotes 99.9%. In the distributions of variation in pulse intervals in FIG. 11B, the distribution ratio based on a vibration signal from the vibration sensor (VS) denotes 39.9% for that of 99.7% based on the electrocardiogram.

In this manner, the distribution ratio of the modal class (M) suggests the presence or absence of "wave skip". In the presence of "wave skip", the distribution ratio reflects how often "wave skip" occurs and is therefore useful as a reference value to determine acceptance or rejection of results in each of the ten types of extraction processing (1 to 10) and to select the best result from those. A larger distribution ratio of the modal class (M) indicates that the extracted set of pulse position candidates is more accurate with fewer occurrences of "wave skip".

A set of pulse position candidates having no occurrences or fewest occurrences of "wave skip" can be selected from 20 sets of pulse position candidates obtained through the extraction processing (1 to 10) by selecting a distribution of variation in pulse intervals or a distribution of the pulse interval having the largest distribution ratio of the modal class (M). With the selected set of pulse position candidates, the stress level can be more accurately calculated.

In the embodiment, both a distribution of the pulse interval and a distribution of variation in pulse intervals are created based on a set of pulse position candidates. The distribution of the pulse interval is likely to get wider with fluctuations in the average heart rate of the subject (S). It is therefore preferable that the distribution of the pulse interval be created in a manner setting a shorter time including comparatively small fluctuations in the average heart rate as the target period (the time necessary to extract effective pulse position candidates from a vibration signal) on the vibration signal from the vibration sensor (VS). The distribution of variation in pulse intervals is less affected by fluctuations in the average heart rate of the subject (S), regardless of the length of the target period on the vibration signal from the vibration sensor (VS). From this viewpoint, a distribution of variation in pulse intervals is more preferably created than a distribution of the pulse interval.

For extracting a set of pulse position candidates from a vibration signal from the vibration sensor (VS), ten types of extraction processing (1 to 10) are performed on both a vibration signal (a body move signal) of the vibration sensor (VS) and a body trunk component extraction signal extracted from the vibration signal to obtain total 20 sets of pulse position candidates. This structure allows a selection of a set of pulse position candidates in a frequency distribution having the best distribution ratio of the modal class among a number of frequency distributions.

Other Embodiments

The embodiment of the present invention may be configured as follows.

The vibration sensor (VS) includes the pressure-sensitive tube (31) and the microphone (36) in this embodiment. The microphone (36) may be replaced with a pressure sensor. The vibration sensor (VS) may include a piezoelectric sheet and a piezoelectric detection circuit or may include an electrostatic sheet and a capacitance detection circuit.

In the embodiment, the pressure-sensitive tube (31) of the vibration sensor (VS) is disposed in the width direction of the sofa (21). In addition to this configuration, another vibration sensor having a pressure-sensitive tube heightwise extending may be disposed in the backrest unit (23), and the ten types of extraction processing (1 to 10) may be performed on each of vibration signals from the vibration sensors and on each of body trunk component extraction signals extracted from those vibration signals.

Furthermore, the microphone (36) of the vibration sensor (VS) is provided to the sensor body (35) in this embodiment. Instead of this configuration, the microphone (36) may be provided at an end of the pressure-sensitive tube (31), and a pressure signal of the microphone (36) may be transmitted to the sensor body (35) through a signal wire.

The subject (S) is seated in the sofa (21) during the examination of the stress level or the autonomic nervous system activity. The subject (S) may be seated in any type of seat furniture including a chair. The subject (S) may be lying on the back or on either side on a sleeping furniture including a bed.

INDUSTRIAL APPLICABILITY

As described above, according to the present invention, a set of pulse position candidates, the largest number of which are extracted on waves corresponding to R-waves of an electrocardiogram, can be selected from a plurality of extracted sets of pulse position candidates. The present invention is therefore useful for a biometric information acquisition device examining the stress level, the autonomic nervous system activity, or the like of a subject.

DESCRIPTION OF REFERENCE CHARACTERS

S Subject (Person)
10 Biological Information Acquisition Device
21 Sofa
31 Pressure-Sensitive Tube
35 Sensor Body
36 Microphone
VS Vibration Sensor (Detection Unit)
37 Pre-Processing Unit
38a to 38t Pulse Position Candidate Extraction Unit (Candidate Extraction Units)
39 Frequency Distribution Calculation Unit (Distribution Calculation Units)
40 Distribution Ratio Calculation Unit
41 Selection Unit
42 Fluctuation Calculation Unit
43 Stress Level Calculation Unit
51 Display Unit

The invention claimed is:

1. A biometric information acquisition device comprising:
    a sensor detecting a vibration including a heartbeat of a person;
    a plurality of candidate extraction units extracting respective sets of pulse position candidates from a target signal that is a signal relating to a vibration signal from the sensor, based on a predetermined specific form;
    a distribution calculation unit calculating a frequency distribution relating to a pulse interval on each of the sets of pulse position candidates extracted by the candidate extraction units;
    a distribution ratio calculation unit calculating a distribution ratio of a modal class to a total frequency on each frequency distribution calculated by the distribution calculation unit; and
    a selection unit selecting a set of pulse position candidates extracted by one of the candidate extraction units using the relative frequencies calculated by the distribution ratio calculation unit as an indicator for evaluating accuracy of the set of pulse position candidates,
    wherein the biometric information acquisition device calculates biometric information on the person on the basis of the selected set of pulse position candidates.

2. The biometric information acquisition device of claim 1, wherein
    the distribution calculation unit calculates a frequency distribution of the pulse interval or a frequency distribution of variation in the pulse interval as a frequency distribution relating to the pulse interval.

3. The biometric information acquisition device of claim 1, wherein
    the selection unit selects a set of pulse position candidates having a largest distribution ratio among a plurality of relative frequencies calculated by the distribution ratio calculation unit.

4. The biometric information acquisition device of claim 1, wherein
    the candidate extraction units include:
        a first candidate extraction unit extracting a set of pulse position candidates from a target signal that is a vibration signal from the sensor; and
        a second candidate extraction unit extracting a set of pulse position candidates from a body trunk component extraction signal generated by extracting a body trunk component from the vibration signal from the sensor.

5. The biometric information acquisition device of claim 1, wherein
    the candidate extraction units include:
        an amplitude-extraction type candidate extraction unit using an amplitude of a wave as the predetermined specific form; and
        a candidate extraction unit using a maximum or a minimum of a wave as the predetermined specific form.

6. The biometric information acquisition device of claim 1, further comprising:
    a fluctuation calculation unit calculating a fluctuation in a pulse interval or in variation in a pulse interval based on the set of pulse position candidates selected by the selection unit; and
    a stress level calculation unit calculating a stress level or an autonomic nervous system activity of the person based on the fluctuation in the pulse interval or in variation in the pulse interval calculated by the fluctuation calculation unit.

* * * * *